(12) United States Patent
Murphy

(10) Patent No.: US 7,576,240 B2
(45) Date of Patent: Aug. 18, 2009

(54) ARYLAMINE PROCESSES

(75) Inventor: Leanne Dawn Murphy, Etobicoke (CA)

(73) Assignee: Xerox Corporation, Norwalk, CT (US)

( * ) Notice: Subject to any disclaimer, the term of this patent is extended or adjusted under 35 U.S.C. 154(b) by 482 days.

(21) Appl. No.: 11/380,339

(22) Filed: Apr. 26, 2006

(65) Prior Publication Data

US 2007/0254225 A1 Nov. 1, 2007

(51) Int. Cl.
*C07C 211/00* (2006.01)

(52) U.S. Cl. ..................................... 564/305

(58) Field of Classification Search .................. None
See application file for complete search history.

(56) References Cited

U.S. PATENT DOCUMENTS

| | | | |
|---|---|---|---|
| 4,265,990 | A | 5/1981 | Stolka et al. |
| 5,324,605 | A * | 6/1994 | Ono et al. .................. 430/58.5 |
| 6,683,025 | B2 | 1/2004 | Amendola et al. |
| 6,730,448 | B2 | 5/2004 | Yoshino et al. |
| 2004/0086794 | A1 | 5/2004 | Yamada et al. |
| 2005/0234272 | A1 | 10/2005 | Goodbrand et al. |

FOREIGN PATENT DOCUMENTS

| | | |
|---|---|---|
| JP | A-57-128344 | 8/1982 |
| JP | B-60-22347 | 6/1985 |
| JP | A-63-65449 | 3/1988 |
| JP | A-04-15659 | 1/1992 |
| JP | B-05-47104 | 7/1993 |
| WO | WO2005044810 | * 10/2004 |

OTHER PUBLICATIONS

Arterburn, J. Tetradedron Letters, 41 (2000) 7847-7849.*
Rajkumar, et al. J. Phys. Chem.A, 2005, 109 2428-2435.*
CRC Handbook of Chemistry and Physics, 89th edition, 2008, 2009, 2-1-25.*
Johnstone et al. Chem. Rev. 1985, 85 (2), 129-170.*
U.S. Appl. No. 10/709,193, filed Apr. 20, 2004, Goodbrand et al.
U.S. Appl. No. 10/992,690, filed Nov. 22, 2004, Bender et al.
U.S. Appl. No. 10/992,687, filed Nov. 22, 2004, Bender et al.
Narisada, M. et al., *Selective Reduction of Aryl Halides and α, β-Unsaturated Esters with Sodium Borohydride-Cuprous Chloride in Methanol and its Application of Deuterium Labeling*, J. Org. Chem., 54, 5308 (1989).
Satoh, T. et al., *Reduction of Organic Compounds with NaBH$_4$-Transition Metal Salt Systems. IV. Selective Hydrogenation of Olefins in Unsaturated Esters*, Chem. & Pharm. Bull., 19(4), 817 (1971).
Sim, T.B. et al., *Selective Reduction of α,β-Unsaturated Acid Derivatives Using Borohydride Exchange Resin-CuSO$_4$ in Methanol*, Synthesis Letters, 7, 726 (1995).
Yoon, N. M., *Selective Reduction of Organic Compounds with Aluminum and Boron Hydrides*, Pure & Appl. Chem. 68 (4), 843 (1996).
Johnstone, R.A.W. et al., *Heterogeneous Catalytic Transfer Hydrogenation and its Relation to Other Methods for Reduction of Organic Compounds*, Chem. Rev. 85, 129 (1985).
Harris, M.C. et al; *One-Pot Synthesis of Unsymmetrical Triarylamines from Aniline Precursors*, J. Org. Chem. 65, 5327 (2000).
Brieger, G. et al., *Catalytic Transfer Hydrogenation*, Chem. Rev. 74(5) 567 (1974).
U.S. Appl. No. 10/992,658, filed Nov. 22, 2004, Goodbrand et al.
U.S. Appl. No. 10/998,585, filed Nov. 30, 2004, Bender et al.
U.S. Appl. No. 11/034,713, filed Jan. 14, 2005, Qi et al.
U.S. Appl. No. 11/094,683, filed Mar. 31, 2005, Goodbrand et al.
U.S. Appl. No. 11/263,371, filed Nov. 1, 2005, Coggan et al.

* cited by examiner

*Primary Examiner*—Daniel M Sullivan
*Assistant Examiner*—Clinton Brooks
(74) *Attorney, Agent, or Firm*—Oliff & Berridge, PLC

(57) ABSTRACT

Processes for selectively hydrogenating double and/or triple bonds in organic molecules include providing at least one organic molecule containing a double and/or triple bond, providing at least one hydrogen donor molecule, and hydrogenating the double and/or triple bond in the presence of at least one catalyst. Processes for preparing arylamine molecules include selectively hydrogenating double bonds in arylamine compounds by providing at least one organic molecule containing a multiple bond, providing at least one hydrogen donor molecule, and hydrogenating the multiple bond in the presence of at least one catalyst. The processes provide efficient, cost-effective and safe methods for conducting selective hydrogenation reactions in the synthesis of organic molecules, such as charge-transport molecules.

18 Claims, 5 Drawing Sheets

ARYLAMINE PROCESSES

RELATED APPLICATIONS

Commonly assigned U.S. Patent Publication Application No. 2007-0100164, describes a process for the preparation of a tertiary arylamine compound, comprising reacting an aryl halide and an arylamine in an ionic liquid in the presence of a catalyst.

Commonly assigned U.S. Patent Publication Application No. 2006-0222977, describes a process for forming an anhydrous alkali earth salt of a dicarboxylic acid of an arylamine compound, comprising reacting a dicarboxylic acid of an arylamine compound with an anhydrous alkali earth salt. The application also discloses a process for forming a siloxane-containing hole-transport molecule, comprising: reacting a dicarboxylic acid of an arylamine compound with an anhydrous alkali earth salt to form an anhydrous dicarboxylic acid salt of the arylamine compound; and reacting the anhydrous dicarboxylic acid salt of the arylamine compound with a siloxane-containing compound.

Commonly assigned U.S. Pat. No. 7,338,739, describes an electrophotographic photoreceptor comprising a charge-generating layer, a charge-transport layer, and an overcoat layer comprised of a crosslinked siloxane composite composition comprising at least one siloxane-containing compound and metal oxide particles.

Commonly assigned U.S. Pat. No. 7,238,456, describes a silicon-containing layer for electrophotographic photoreceptors comprising: one or more siloxane-containing compound; and one or more siloxane-containing antioxidant; wherein the siloxane-containing antioxidant is at least one member selected from the group consisting of hindered-phenol antioxidants, hindered-amine antioxidants, thioether antioxidants and phosphite antioxidants.

Commonly assigned U.S. Pat. No. 7,402,699, describes a process for forming a tertiary arylamine compound, comprising reacting an arylbromide and an arylamine. For example, the application describes a process for forming N,N-diphenyl-4-aminobiphenyl, comprising reacting 4-bromobiphenyl and diphenylamine in the presence of a palladium-ligated catalyst.

Commonly assigned U.S. Pat. No. 7,227,034, describes a process for forming a 4-aminobiphenyl derivative arylamine compound, comprising: (i) providing a first disubstituted 4-aminobiphenyl compound; (ii) optionally formylating the first disubstituted 4-aminobiphenyl compound to form a bisformyl substituted compound, where the first disubstituted 4-aminobiphenyl compound is not a bisformyl substituted compound; (iii) acidifying the bisformyl substituted compound to convert formyl functional groups into acid functional groups to form an acidified compound; and (iv) hydrogenating the acidified compound to saturate at least one unsaturated double bonds in the acidified compound, wherein there is provided a second disubstituted 4-aminobiphenyl compound.

Commonly assigned U.S. Pat. No. 7,196,214, describes a process for forming a 4-aminobiphenyl derivative arylamine compound, comprising: (i) providing an iodinated organic compound; (ii) substituting the iodinated organic compound at carboxylic acid groups thereof to provide ester protecting groups; (iii) conducting an Ullman condensation reaction to convert the product of step (ii) into an arylamine compound; and (iv) conducting a Suzuki coupling reaction to add an additional phenyl group to the arylamine compound in the 4-position relative to the nitrogen, to provide the 4-aminobiphenyl derivative arylamine compound.

Commonly assigned U.S. patent application Ser. No. 10/709,193, filed Apr. 20, 2004, which published as U.S. Patent Application Publication No. 2005-0234272 on Oct. 20, 2005, describes a process for preparing an aryl iodide compound, comprising: reacting an aryl halide compound with a metal iodide, a metal catalyst and a catalyst coordinating ligand in at least one solvent to form an aryl iodide; and purifying the aryl iodide; wherein the solvent is heated to reflux during the reacting; wherein an aryl iodide yield of at least about 75% is obtained; and wherein the aryl iodide has a purity of at least 90%.

The appropriate components and process aspects of each of the foregoing, such as the arylamine precursor materials and electrophotographic imaging members, may be selected for the present disclosure in embodiments thereof. The entire disclosures of the above-mentioned applications are totally incorporated herein by reference.

TECHNICAL FIELD

This disclosure is generally directed to processes for the synthesis of arylamine compounds, and to the use of such compounds in electrophotographic imaging members. In particular, this disclosure provides processes for the selective hydrogenation of unsaturated arylamine compounds.

REFERENCES

JP-A-63-65449 (the term "JP-A" as used herein means an "unexamined published Japanese patent application"), discloses an electrophotographic photoreceptor in which fine silicone particles are added to a photosensitive layer and also discloses that such addition of the fine silicone particles imparts lubricity to a surface of the photoreceptor.

Further, in forming a photosensitive layer, a method has been proposed in which a charge transport substance is dispersed in a binder polymer or a polymer precursor thereof, and then the binder polymer or the polymer precursor thereof is cured. JP-B-5-47104 (the term "JP-B" as used herein means an "examined Japanese patent publication") and JP-B-60-22347, disclose electrophotographic photoreceptors using silicone materials as the binder polymers or the polymer precursors thereof.

Furthermore, in order to improve mechanical strength of the electrophotographic photoreceptor, a protective layer is formed on the surface of the photosensitive layer in some cases. A cross-linkable resin is used as a material for the protective layer in many cases. However, the protective layer formed by the cross-linkable resin acts as an insulating layer, which impairs the photoelectric characteristics of the photoreceptor. For this reason, a method of dispersing a fine conductive metal oxide powder (JP-A-57-128344) or a charge-transport substance (JP-A-4-15659) in the protective layer and a method of reacting a charge-transport substance having a reactive functional group with a thermoplastic resin to form the protective layer have been proposed.

However, even the above-mentioned conventional electrophotographic photoreceptors are not necessarily sufficient in electrophotographic characteristics and durability, particularly when used in combination with a charger of the contact-charging system (contact charger) or a cleaning apparatus, such as a cleaning blade.

Further, when a photoreceptor is used in combination with a contact charger and a toner obtained by chemical polymerization (polymerization toner), a surface of the photoreceptor may become stained with a discharge product produced in contact charging or with polymerization toner that remains after a transport step. This staining can deteriorate image quality in some cases. Still further, use of a cleaning blade to remove discharge product or remaining toner adhered to the photoreceptor surface increases friction and abrasion between the surface of the photoreceptor and the cleaning blade, resulting in a tendency to cause damage to the surface of the photoreceptor, breakage of the blade or turning up of the blade.

Furthermore, in producing a photoreceptor, in addition to improvement in electrophotographic characteristics and durability, reducing production costs becomes an important problem. However, conventional electrophotographic photoreceptors also may have problems relating to coating defects such as orange-peel appearances and hard spots.

The use of silicon-containing compounds in photoreceptor layers, including in photosensitive and protective layers, has been shown to increase the mechanical lifetime of electrophotographic photoreceptors, under charging conditions and scorotron charging conditions. For example, U.S. Patent Application Publication US 2004/0086794 to Yamada et al. discloses a photoreceptor having improved mechanical strength and stain resistance.

However, the above-mentioned conventional electrophotographic photoreceptor is not necessarily sufficient in electrophotographic characteristics and durability, particularly when such a photoreceptor is used in an environment of high heat and humidity.

Photoreceptors having low wear rates, such as those described in Yamada, also have low refresh rates. The low wear and refresh rates are a primary cause of image-deletion errors, particularly under conditions of high humidity and high temperature. U.S. Pat. No. 6,730,448 B2 to Yoshino at al. addresses this issue, disclosing photoreceptors having some improvement in image quality, fixing ability, even in an environment of high heat and humidity. However, there still remains a need for electrophotographic photoreceptors having high mechanical strength and improved electrophotographic characteristics and improved image-deletion characteristics even under conditions of high temperature and high humidity.

Over the past several years, Buchwald et al. (MIT) and Hartwig et al. (Yale) have both reported on the general versatility of palladium-based catalysts for the formation of nitrogen-carbon bonds. Their work has focused on the arylation of alkylamine and alkylamides, but they have reported the use of palladium-based catalysts for arylamine synthesis starting from an aryl bromide or an aryl chloride. See Harris, M. C. et al; *One-Pot Synthesis of Unsymmetrical Triarylamines from Aniline Precursors, J. Org. Chem.*, 65, 5327 (2000).

Brieger, G. et al., *Catalytic Transfer Hydrogenation, Chemical Reviews* 74(5) 567 (1974), and Johnstone, R. A. W. et al., Heterogeneous Catalytic Transfer Hydrogenation and its Relation to Other Methods for Reduction of Organic Compounds, Chem. Rev. 85, 129 (1985), describe transfer hydrogenation-dehydrogenation reactions in which hydrogen is removed from donor molecules and selectively added to acceptor molecules in the presence of a catalysts.

Narisada, M. et al., *Selective Reduction of Aryl Halides and α, β-Unsaturated Esters with Sodium Borohydride-Cuprous Chloride in Methanol and its Application of Deuterium Labeling, J. Org. Chem.*, 54, 5308 (1989); Sato, T. et al., *Reduction of Organic Compounds with $NaBH_4$-Transition Metal Salt Systems, IV, Selective Hydrogenation of Olefins in Unsaturated Esters, Chem. & Pharm. Bull.*, 19(4), 817 (1971); Sim, T. B. et al., *Selective Reduction of α,β-Unsaturated Acid Derivatives Using Borohydride Exchange Resin-$CuSO_4$ in Methanol, Synthesis Letters*, 7, 726 (1995); and Yoon, N. M. *Selective Reduction of Organic Compounds with Aluminum and Boron Hydrides, Pure & Appl. Chem.* 68 (4), 843 (1996), describe metal hydride—transition metal salt catalytic systems that selectively reduce carbon-carbon double bonds.

U.S. Pat. No. 6,683,025 B2 to Amendola et al. describes processes for making hydrogen generation catalysts. In particular, the patent discloses a process for producing a supported hydrogen generation catalyst comprising: contacting an anionic exchange resin substrate with a solution comprising an anionic complex of a transition metal ion, said complex represented by the formula $(M^y+X_6)^{y-6}$), wherein M is a transition metal, y is the valence of the transition metal, and X is an anion with a single negative charge, thereby effecting an exchange reaction whereby the anion associated with the exchange resin is substituted with the anion of said transition metal complex, wherein said solution is obtained by dissolving a transition metal salt in an acid to form said complex, further wherein the anion of said acid corresponds to the anion of said transition metal salt; and contacting the resulting anionic exchange resin substrate with a reducing agent.

The disclosures of each of the foregoing patents and publications, and the disclosures of any patents and publications cited below, are hereby totally incorporated by reference. The appropriate components and process aspects of the each of the cited patents and publications may also be selected for the present compositions and processes in embodiments thereof.

BACKGROUND

In electrophotography, an electrophotographic substrate containing a photoconductive insulating layer on a conductive layer is imaged by first uniformly electrostatically charging a surface of the substrate. The substrate is then exposed to a pattern of activating electromagnetic radiation, such as, for example, light. The electromagnetic radiation selectively dissipates charge in illuminated areas of the photoconductive insulating layer while leaving behind an electrostatic latent image in non-illuminated areas of the photoconductive insulating layer. This electrostatic latent image is then developed to form a visible image by depositing finely divided electroscopic marking particles on the surface of the photoconductive insulating layer. The resulting visible image is then transferred from the electrophotographic substrate to a necessary member, such as, for example, an intermediate-transfer member or a print substrate, such as paper. This image developing process can be repeated as many times as necessary with reusable photoconductive insulating layers.

In image-forming apparatus such as copiers, printers and facsimiles, electrophotographic systems in which charging, exposure, development, transfer, etc. are carried out using electrophotographic photoreceptors have been widely employed. In such image-forming apparatus, there are ever-increasing demands for speeding up of image-formation processes, improvement in image quality, miniaturization and prolonged life of the apparatus, reduction in production cost and running cost, etc. Further, with recent advances in computers and communication technology, digital systems and color-image output systems have been applied also to the image-forming apparatus.

Electrophotographic imaging members (photoreceptors) are known. Electrophotographic imaging members are commonly used in electrophotographic processes having either flexible-belt or rigid-drum configurations. These electrophotographic imaging members sometimes comprise a photoconductive layer including a single layer or composite layers.

These electrophotographic imaging members take many different forms. For example, layered photo-responsive imaging members are known in the art. U.S. Pat. No. 4,265,990 to Stolka et al. describes a layered photoreceptor having separate photogenerating and charge-transport layers. The photogenerating layer disclosed in Stolka is capable of photogenerating holes and injecting the photogenerated holes into the charge-transport layer. Thus, in the photoreceptors of Stolka, the photogenerating material generates electrons and holes when subjected to light.

More advanced photoconductive photoreceptors containing highly specialized component layers are also known. For example, a multi-layered photoreceptor employed in electrophotographic imaging systems sometimes includes one or more of a substrate, an undercoating layer, an intermediate layer, an optional hole- or charge-blocking layer, a charge-generating layer (including a photogenerating material in a binder) over an undercoating layer and/or a blocking layer, and a charge-transport layer (Including a charge-transport material in a binder). Additional layers such as one or more overcoat layer or layers are also sometimes included.

In view of such a background, improvement in electrophotographic properties and durability, miniaturization, reduction in cost, and the like, in electrophotographic photoreceptors have been studied, and electrophotographic photoreceptors using various materials have been proposed.

Production of a number of arylamine compounds, such as arylamine compounds that are useful as charge-transport compounds in electrostatographic imaging devices and processes, often involves synthesis of intermediate materials, some of which generally are costly and/or time-consuming to produce, and some of which involve a multi-step process. One such intermediate product is the arylamine N,N-di(4-propanoic acid)-4-aminobiphenyl, which is itself useful as a charge-transport compound in electrostatographic imaging devices and processes. Even production of this intermediate compound currently involves a long, costly process.

Currently, arylamine-derivative hole-transporting molecules are prepared by a process that includes reducing or hydrogenating a double bond using compressed hydrogen gas. For example, N,N-di(4-propanoic acid)-4-aminobiphenyl has been produced by selectively reducing N,N-di(4-propenoic acid)-4-aminobiphenyl using compressed hydrogen ($H_2$) gas. While known and useful on a small, laboratory scale, this method is not conducive to large scale production of arylamine-derivative hole-transporting molecules, because it is costly and poses safety concerns.

First, hydrogen gas is a highly diffusible and highly combustible gas. The safety requirements for equipment and facilities for using hydrogen gas are strict, and altering equipment and facilities to meet or exceed the safety requirements for larger scale hydrogenation reactions could be very costly, particularly in light of the small volume necessary for the preparation of arylamine molecules.

Second, the efficiency of conventional hydrogenation reactions using compressed hydrogen gas depends on converting large amounts of the hydrogen gas to the liquid phase. In order to increase efficiency, elevated pressure and temperature, which would require specialized mixing equipment, would be necessary, and would, in turn, increase production costs.

Accordingly, improved processes providing safe, cost-effective and efficient methods for selective hydrogenation are desired for producing arylamines, such as N,N-di(4-propanoic acid)-4-aminobiphenyl, and similar compounds.

SUMMARY

The present disclosure addresses these and other needs, by providing processes that include selective hydrogenation of organic molecules by catalytic transfer hydrogenation processes to avoid problems and costs associated with reduction by compressed hydrogen gas. Such processes can achieve safer synthetic processes without requiring costly upgrades to equipment and facilities, and can enable selective hydrogenation to be performed in standard equipment.

Exemplary methods include processes for selectively hydrogenating double and/or triple bonds in organic molecules, comprising: providing one or more acceptor molecules that contains one or more double bonds and/or one or more triple bonds; providing one or more hydrogen donor molecules; and hydrogenating the double bonds and/or the triple bonds of the organic molecules in the presence of one or more catalysts.

Additional exemplary methods include processes for preparing arylamine molecules, comprising: selectively hydrogenating double bonds in arylamine compounds, wherein selectively hydrogenating double bonds comprises: providing one or more arylamine compounds that contains one or more double bonds and/or one or more triple bonds; providing one or more hydrogen donor molecules; and hydrogenating the double bonds and/or the triple bonds of the arylamine compounds in the presence of one or more catalysts.

In addition, embodiments include electrophotographic imaging members comprising: a substrate; a charge-generating layer; a charge-transport layer; and optionally an overcoating layer; wherein the charge-transporting layer includes one or more charge-transporting molecules prepared by a process that comprises: providing one or more acceptor molecules that contains one or more double bonds and/or one or more triple bonds; providing one or more hydrogen donor molecules; and hydrogenating the double bonds and/or the triple bonds of the organic molecules in the presence of one or more catalysts.

These and other features and advantages of various embodiments of materials, devices, systems and/or methods are described in or are apparent from, the following detailed description.

EMBODIMENTS

Figure 1:
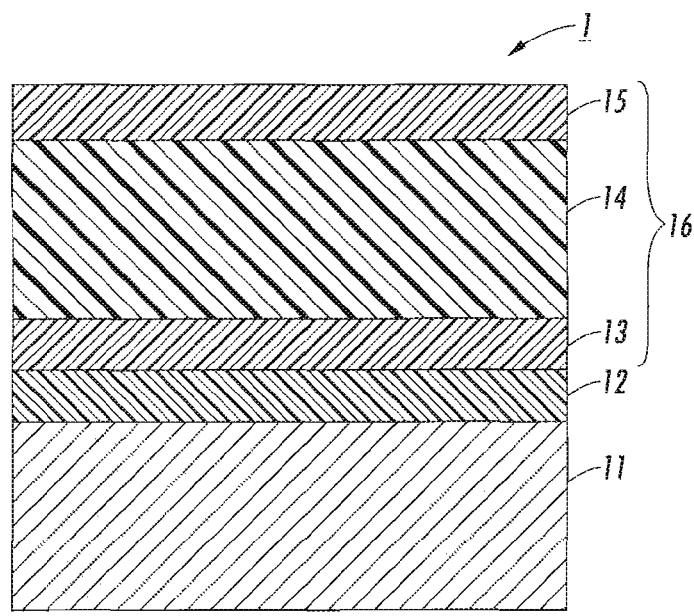
FIG. 1 is a schematic cross sectional view showing an embodiment of an electrophotographic photoreceptor of the disclosure.

This disclosure is not limited to particular embodiments described herein, and some components and processes may be varied by one of skill, based on this disclosure. The terminology used herein is for the purpose of describing particular embodiments only, and is not intended to be limiting.

In this specification and the claims that follow, singular forms such as "a," "an," and "the" include plural forms unless the content clearly dictates otherwise. In addition, reference may be made to a number of terms that shall be defined as follows:

The term "organic molecule" refers, for example, to any molecule that is made up predominantly of carbon and hydrogen, such as, for example, alkanes and arylamines. The term "heteroatom" refers, for example, to any atom other than carbon and hydrogen. Typical heteroatoms included in organic molecules include oxygen, nitrogen, sulfur and the like.

The term "saturated" refers, for example, to compounds containing only single bonds. The term "unsaturated" refers, for example, to compounds that contain one or more double bonds and/or one or more triple bonds.

The terms "hydrocarbon" and "alkane" refer, for example, to branched and unbranched organic molecules having the general formula $C_nH_{2n+2}$, in which n is a number of 1 or more, such as of from about 1 to about 60. Exemplary alkanes include methane, ethane, n-propane, isopropane, n-butane, isobutane, tert-butane, octane, decane, tetradecane, hexadecane, eicosane, tetracosane and the like. Alkanes may be substituted by replacing hydrogen atoms with one or more functional groups.

The term "aliphatic" refers, for example, to straight-chain molecules, and may be used to describe acyclic, unbranched alkanes.

The term "long-chain" refers, for example, to hydrocarbon chains in which n is a number of from about 8 to about 60, such as from about 20 to about 45 or from about 30 to about 40. The term "short-chain" refers, for example, to hydrocarbon chains in which n is a number of from about 1 to about 7, such as from about 2 to about 5 or from about 3 to about 4.

The term "alkyl" refers, for example, to a branched or unbranched saturated hydrocarbon group, derived from an alkane and having the general formula $C_nH_{2n+1}$, in which n is a number of 1 or more, such as of from about 1 to about 60. Exemplary alkyl groups include methyl, ethyl, n-propyl, isopropyl, n-butyl, isobutyl, tert-butyl, octyl, decyl, tetradecyl, hexadecyl, eicosyl, tetracosyl and the like. The term "lower alkyl" refers, for example, to an alkyl group of from about 1 to about 12 carbon atoms. "Halogenated alkyl" refers, for example, to an alkyl group in which at least one hydrogen atom, and optionally all hydrogen atoms, is replaced by a halogen atom.

The term "aromatic" refers, for example, to an organic molecule or radical in which some of the bonding electrons are delocalized or shared among several atoms within the molecule and not localized in the vicinity of the atoms involved in the bonding. Aromatic compounds may include heteroatoms in the molecules, and may include one or more cyclic or ring systems that may include one or more fused aromatic rings. Examples of aromatic compounds include, for example, benzene ($C_6H_6$), naphthalene ($CH_{10}H_8$), anthracene ($C_{14}H_{10}$), pyridine ($C_5H_5N$) and the like. Optionally, these aromatic compounds may be substituted with one or more independently selected substituents, including alkyl, alkenyl, alkoxy, aryl, hydroxyl and nitro groups.

The term "aryl" refers, for example, to an organic group derived from an aromatic compound and having the same general structure as the aromatic compound. Examples of aromatic compounds include, for example, phenyl ($C_6H_5$), benzyl ($C_7H_7$), naphthyl ($C_{10}H_7$), anthracyl ($C_{14}H_9$), pyridinyl ($C_5H_4N$) and the like. Optionally, these aromatic groups may be substituted with one or more independently selected substituents, including alkyl, alkenyl, alkoxy, aryl, hydroxyl and nitro groups.

The term "arylamine" refers, for example, to moieties containing both aryl and amine groups. Exemplary aralkylene groups have the structure Ar—NRR', in which Ar represents an aryl group and R and R' are groups that may be independently selected from hydrogen and substituted and unsubstituted alkyl, alkenyl, aryl and other suitable functional groups. The term "triarylamine" refers, for example, to arylamine compounds having the general structure NArAr'Ar", in which Ar, Ar' and Ar' represent independently selected aryl groups.

The term "alcohol" refers, for example, to an alkyl moiety in which one or more of the hydrogen atoms has been replaced by an —OH group. The term "lower alcohol" refers, for example, to an alkyl group of about 1 to about 6 carbon atoms in which at least one, and optionally all, of the hydrogen atoms has been replaced by an —OH group. The term "primary alcohol" refers, for example to alcohols in which the —OH group is bonded to a terminal or chain-ending carbon atom, such as in methanol, ethanol, 1-propanol, 1-butanol, 1-hexanol and the like. The term "secondary alcohol" refers, for example to alcohols in which the —OH group is bonded to a carbon atom that is bonded to one hydrogen atom and to two other carbon atoms, such as in 2-propanol (isopropanol), 2-butanol, 2-hexanol and the like. The term "tertiary alcohol" refers, for example to alcohols in which the —OH group is bonded to a carbon atom that is bonded to three other carbon atoms, such as in methylpropanol (tert-butanol) and the like.

The term "amine" refers, for example, to an alkyl moiety in which one or more of the hydrogen atoms has been replaced by an —$NH_2$ group. The term "lower amine" refers, for example, to an alkyl group of about 1 to about 6 carbon atoms in which at least one, and optionally all, of the hydrogen atoms has been replaced by an —$NH_2$ group.

The term "carbonyl compound" refers, for example, to an organic compound containing a carbonyl group, C=O, such as, for example, aldehydes, which have the general formula RCOH; ketones, which have the general formula RCOR'; carboxylic acids, which have the general formula RCOOH; and esters, which have the general formula RCOOR'.

The term "derivative" refers, for example, to compounds that are derived from another compound and maintain the same general structure as the compound from which they are derived. For example, saturated alcohols and saturated amines are derivatives of alkanes.

The term "homologous" refers, for example, to any number of series of organic compounds that have similar chemical properties and that differ by a constant relative molecular mass. For example, lower alcohols are a homologous series that includes $CH_3OH$, $CH_3CH_2OH$, $CH_3CH_2CH_2OH$, $CH_3(CH_2)_2CH_2OH$, $CH_3(CH_2)_3CH_2OH$ and $CH_3(CH_2)_4CH_2OH$, as well as isomers of these molecules.

The term "reflux" refers, for example, to the process of boiling, a liquid, condensing the vapor and returning the vapor to the original container. When a liquid is refluxed, the temperature of the boiling liquid remains constant. The term "boiling point" refers, for example, to the temperature at which the saturated vapor pressure of a liquid is equal to the external atmospheric pressure.

The terms "standard temperature" and "standard pressure" refer, for example, to the standard conditions used as a basis where properties vary with temperature and/or pressure. Standard temperature is 0° C.; standard pressure is 101,325

Pa or 760.0 mmHg. The term "room temperature" refers, for example, to temperatures in a range of from about 20° C. to about 25° C.

The terms "high temperature environment" and "high temperature conditions" refer, for example, to an atmosphere in which the temperature is at least about 28 or about 30° C., and may be as high as about 300° C. The terms "high humidity environment" and "high humidity conditions" refer, for example, to an atmosphere in which the relative humidity is at least about 75 or about 80%.

The terms "selective" and "selectively" refer, for example, to reactions in which the reaction occurs at only one reaction site of multiple possible reaction sites where such a reaction could theoretically occur. For example, a selective hydrogenation reaction of a propenoic acid compound may add hydrogen across only the carbon-carbon double bond, and not across the carbon-oxygen double bond, to form a propanoic acid compound.

The terms "optional" and "optionally" refer, for example, to instances in which subsequently described circumstance may or may not occur, and include instances in which the circumstance occurs and instances in which the circumstance does not occur.

The terms "one or more" and "at least one" refer, for example, to instances in which one of the subsequently described circumstances occurs, and to instances in which more than one of the subsequently described circumstances occurs.

In a catalytic transfer-hydrogenation reaction, hydrogen is transferred from a donor molecule to an acceptor molecule. The release of hydrogen from the donor requires a catalyst that transfers the hydrogen to the acceptor. That is, the catalyst abstracts the hydrogen from the donor molecule. This is illustrated below as exemplary reaction (1). In reaction (1), hydrogen is removed from ammonium formate, shown here as formyl and ammonium ions. The products of this reaction are $CO_2$, $NH_3$ and $H_2$, all of which are non-toxic and can be easily removed from the system.

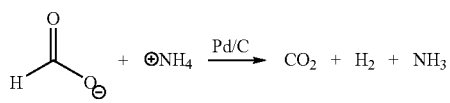

(1)

Once hydrogen has been removed from the donor molecule, it may be transferred to an acceptor molecule. That is, hydrogen ions abstracted from the donor molecule react to reduce a multiple bond in the acceptor molecule, resulting in cis-addition of hydrogen across a double or triple bond in the acceptor molecule.

The acceptor molecule in embodiments of catalytic transfer hydrogenation processes disclosed herein may be any organic molecule that contains one or more alkyl groups having one or more double bond and/or one or more triple bond. In embodiments, acceptor molecules may be any suitable arylamine, depending on the desired final product, that includes one or more double bond and/or one or more triple bond to be reduced. For example, the arylamine may correspond to the exemplary triarylamine (A) below. Triarylamine (A) includes substituents $R^1$-$R^{15}$, which can be the same or different, can be suitably selected to represent hydrogen, a halogen, an alkyl group having for example from 1 to about 20 carbon atoms, an aryl group optionally substituted by one or more alkyl groups, an alkyl group containing a heteroatom, an aryl group containing a heteroatom and optionally substituted by one or more alkyl groups, and the like, as long as at least one of $R^1$-$R^{15}$ includes a multiple bond. In embodiments, the arylamine is a diphenylamine derivative.

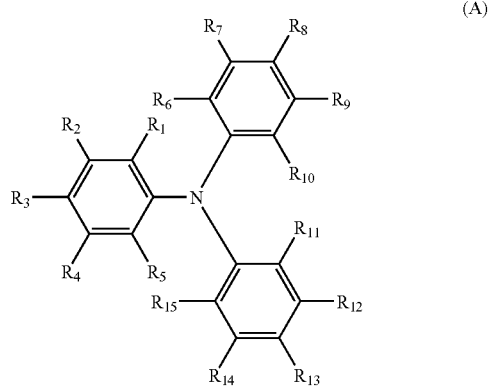

(A)

In embodiments, one or more of $R^6$-$R^{15}$ of the arylamine may include an acrylic acid group, which may be selectively hydrogenated by catalytic transfer hydrogenation. Suitable acrylic acid-containing arylamines may include N,N-di(4-propenoic acid)-4-aminobiphenyl and homologous molecules. The organic acceptor molecule of embodiments may be one organic acceptor molecule as described above or may be a mixture of two or more such organic acceptor molecules.

In embodiments, the acceptor molecule may be reacted in any suitable amount to obtain the desired product.

In embodiments, the donor molecule of catalytic transfer hydrogenation processes disclosed herein may be an organic donor molecule. Suitable donor molecules include organic compounds that may be oxidized under mild conditions. The term "mild conditions" refers, for example, to conditions having a temperature of from about 0° C. to about 100° C., such as from about 25° C. to about 85° C. or from about 50° C. to about 65° C.; and standard pressure.

The donor molecules are not otherwise particularly limited. Non-limiting examples of suitable donor molecules include hydrazine; formic acid and formates, such as ammonium formate; substituted and unsubstituted cyclohexenes; substituted and unsubstituted octalins; substituted and unsubstituted tetralins, substituted and unsubstituted pinenes; substituted and unsubstituted carenes; substituted and unsubstituted phellandrenes; substituted and unsubstituted terpinolenes; substituted and unsubstituted menthenes; substituted and unsubstituted cadalene; substituted and unsubstituted pulegones; substituted and unsubstituted selinenes; and alcohols, such as methanol, ethanol, 2-propanol, octanol, diethylcarbinol, cyclohexanol, benzyl alcohol, phenylethanols, cyclohexylphenols and the like. See Brieger, at 568. The donor molecule of embodiments may be one such donor molecule or may be a mixture of two or more such donor molecules.

In embodiments, the donor molecule may be reacted in amounts from about 1 to about 4 molar equivalents, or from about 1 to about 2.5 molar equivalents weight, per molar equivalent of acceptor molecule.

The reactants are reacted in the presence of a suitable catalyst or combination of catalysts. Although not particularly limited, suitable catalysts are those that are known or discovered to be useful for selective hydrogenation of multiple bonds. For example, suitable catalysts for use in embodiments include palladium-based catalysts, such as Pd black, Pd/C, Pd/CaCO$_3$, Pd/Al$_2$O$_3$, Pd/Pt, ligated palladium catalysts and the like; Pt black; Pt/C; Raney Ni and the like, as well as mixtures thereof. The above-mentioned palladium-based catalysts are particularly suitable for some embodiments.

Alternatively, the catalyst of embodiments may be chosen from homogeneous catalysts. Suitable homogeneous catalysts include ruthenium complexes, such as RuCl$_2$(Ph$_3$P)$_3$; iridium complexes, such as HIrCl$_2$I(Me$_2$SO)$_3$, Ir(CO)Br(Ph$_3$P)$_2$; rhodium complexes, such as RhCl(Ph$_3$As)$_2$; and platinum complexes, such as PtCl$_2$(Ph$_3$As)$_2$+SnCl$_2$.H$_2$O.

The catalyst of embodiments may be one catalyst chosen from palladium-based catalysts, such as Pd black, Pd/C, Pd/CaCO$_3$, Pd/Al$_2$O$_3$, Pd/Pt and the like; Pt black; Pt/C; Raney Ni; ruthenium complexes, such as RuCl$_2$(Ph$_3$P)$_3$; iridium complexes, such as HIrCl$_2$(Me$_2$SO)$_3$, Ir(CO)Br(Ph$_3$P)$_2$; rhodium complexes, such as RhCl(Ph$_3$As)$_2$; and platinum complexes, such as PtCl$_2$(Ph$_3$As)$_2$+SnCl$_2$.H$_2$O; and the like. In embodiments, the catalyst may be a mixture of two or more such catalysts.

As an example, reaction (2) below illustrates an embodiment in which an exemplary arylamine, N,N-di(propenoic acid)-4-aminobiphenyl (Compound B), is selectively hydrogenated by catalytic transfer hydrogenation using ammonium formate as a donor molecule and Pd/C as the catalyst. The reaction selectively reduces the double bonds in the acrylic acid portions of the N,N-di(propenoic acid)-4-aminobiphenyl (Compound B) to produce N,N-di(propanoic acid)-4-aminobiphenyl (Compound C).

embodiments, the catalyst may be chosen from catalytic systems such as, for example, metal hydride—transition metal salt catalyst systems.

It is well known that metal hydrides are useful for reducing functional groups in organic molecules. Used alone, metal hydrides show very little specificity in reducing functional groups; although individual metal hydrides may have distinct sets of functional groups that they are capable of reducing. For example, sodium borohydride, NaBH$_4$, will reduce only a very narrow range of organic functional groups, while lithium aluminum hydride, LiAlH$_4$, will reduce most organic functional groups. However, when metal hydrides are combined with transition metal salts, selective hydrogenation of carbon-carbon double bonds (C=C) in unsaturated ester molecules may be achieved. That is, selective catalysts that may be used in embodiments of processes disclosed herein include catalyst systems prepared from the reaction of a metal hydride and a transition metal salt, which may produce a black, granular material believed to be an active catalyst for selective hydrogenation of carbon-carbon double bonds (C=C) in α,β-unsaturated ester molecules.

The metal hydrides of metal hydride—transition metal salt catalyst systems of embodiments may have the general chemical formula MYH$_4$. In this formula, M may be chosen from alkali metals, such as, for example, elements of Group 1 (formerly Group IA) of the periodic table, including lithium (Li), sodium (Na), potassium (K), and the like; and organic functional groups, such as, for example, ammonium groups and the like. Y in the formula MYH$_4$ is an element chosen

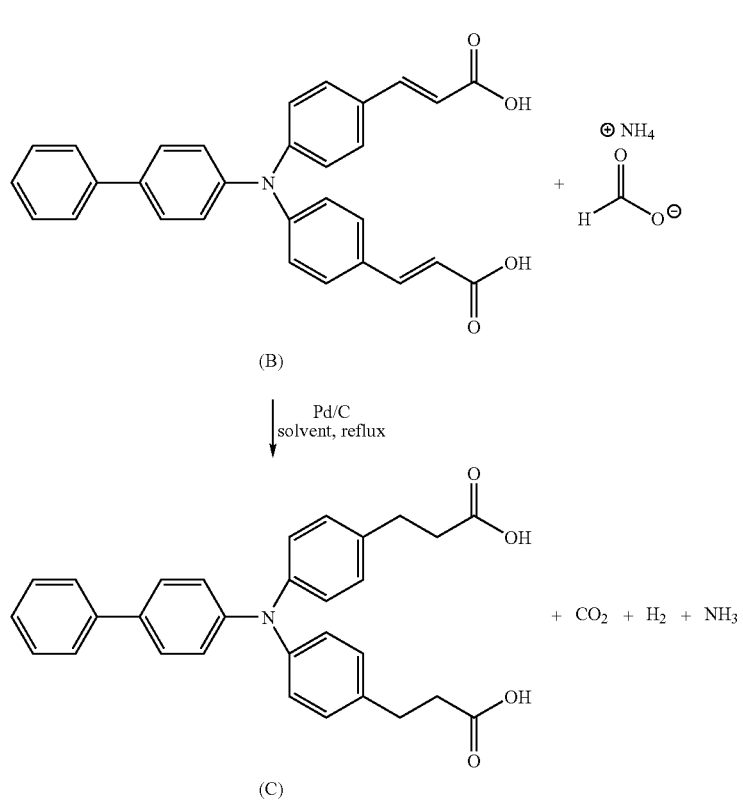

(2)

However, the catalysts set forth above may be pyrophoric, such as for example, palladium on carbon (Pd/C), and may be dangerous when used in large scale reactions. Thus, in some from Group 13 (formerly Group IIIA) of the periodic table, including boron (B), aluminum (Al), gallium (Ga), and the like. Examples of metal hydrides that may be used in the metal hydride—transition metal salt catalyst systems of embodiments include NaBH$_4$, LiBH$_4$, KBH$_4$, NH$_4$BH$_4$, (CH$_3$)$_4$NBH$_4$, NaAlH$_4$, LiAlH$_4$, KAlH$_4$, NaGaH$_4$, LiGaH$_4$, KGaH$_4$, and the like, and mixtures thereof. In some embodiments, the metal hydride is chosen from borohydrides and mixtures thereof; and in certain of these embodiments, the metal hydride is one or more borohydride chosen from sodium borohydride (NaBH$_4$), lithium borohydride (LiBH$_4$), potassium borohydride (KBH$_4$), ammonium borohydride (NH$_4$BH$_4$), tetramethyl ammonium borohydride ((CH$_3$)$_4$NBH$_4$), quaternary borohydrides, and mixtures thereof.

Alternatively, ion exchange resins may be used as the metal hydride in embodiments. Ion exchange resins are porous polymeric materials having active groups at the end of the polymer chains. The polymer chains of ion exchange resins include polystyrene, epoxy amines, epoxy polyamines, phenolics, and acrylics. Ion exchange resins are classified into anionic exchange resins and cationic exchange resins, and are commercially available.

Anionic exchange resins have positively charged active groups at the ends of the polymers. Non-limiting examples of positively charged active groups include a quaternary ammonium, tertiary amine, trimethyl benzyl ammonium, and/or dimethyl ethanol benzyl ammonium. Commercially available anionic exchange resins include A-26, A-36, IRA-400 and IRA-900, manufactured by Rohm & Haas, Inc. DOWEX 1. DOWEX 2, DOWEX 21 K, DOWEX 550A, DOWEX MSA-1, and DOWEX MSA-2, manufactured by Dow Corporation; DUOLITE A-101 D, DUOLITE A-102 D, and DUOLITE A-30 B; and IONAC A-540 IONAC A-550, and IONAC A-300.

Cationic exchange resins nave negatively charged active groups at the ends of the polymers. Non-limiting examples of negatively charged active groups include sulfonic acid, carboxylic acid, phosphonic acid, and/or aliphatic acid. Commercially available cationic exchange resins include, but are not limited to, NAFION resins, manufactured by Dupont Corp.; IRA-120 and AMBERLYST 15 manufactured by Rohm & Haas, Inc.; DOWEX 22, DOWEX 50, DOWEX 88, DOWEX MPC-1, and DOWEX HCR-W2 and DOWEX CCR-1, manufactured by Dow Corporation; DUOLITE C-3, DUOLITE ES-63, and DUOLITE ES-80; and IONAC 240.

The transition metal salts of the metal hydride—transition metal salt catalyst systems of embodiments may be any suitable salts of transition metal elements, which are elements of Groups 3 through 12 (formerly Groups IIIB through IIB) of the periodic table. Representative examples of transition metals that may be useful in embodiments include elements in the scandium, titanium, vanadium, chromium, manganese, iron, cobalt, nickel, copper and zinc, groups. In embodiments, the transition metal of the transition metal salts may be one or more of ruthenium, iron, cobalt, nickel, copper, manganese, rhodium, rhenium, platinum, palladium, chromium, silver, osmium, iridium, borides thereof, alloys thereof, and mixtures thereof. Non-limiting examples of suitable transition metal salts for use in embodiments include Cu$_2$Cl$_2$, CuCl$_2$, CoCl$_2$, PdCl$_2$, CuSO$_4$, and the like, and mixtures thereof.

In embodiments in which a metal hydride—transition metal salt catalyst system is employed, the metal hydride may be added slowly, to prevent H$_2$ build-up within the reaction system and to prevent the reaction from becoming exothermic. This may be accomplished, in some such embodiments, by dissolving the metal hydride in a solvent that contains a metal hydride stabilizing agent. Herein, the term "metal hydride stabilizing agent" refers to any component that retards, impedes, or prevents reaction of metal hydride with the solvent, which may be water in embodiments. Suitable metal hydride stabilizing agents may be hydroxide salts that are dissolved in a solvent prior to addition of the metal hydride. Examples of hydroxide salts for use in embodiments include sodium hydroxide (NaOH), lithium hydroxide (LiOH), potassium hydroxide (KOH), and the like and mixtures thereof. Examples of solvents for dissolving metal hydride stabilizing agents in embodiments include water; short chain alcohols, such as methanol, ethanol, propanol, butanol and the like; polar aprotic solvents, such as dimethylformamide (DMF), dimethyl sulfoxide (DMSO), acetone, ethyl acetate, tetrahydrofuran (THF), methyl ethyl ketone (MEK) and the like; and mixtures thereof. In embodiments, for example, the solvent may be a mixture of methanol and tetrahydrofuran.

It should be understood that the metal hydride—transition metal salt catalyst systems described herein may be used individually, or as mixtures of multiple metal hydride—transition metal salt catalyst systems.

An exemplary, generalized reaction in which a metal hydride—transition metal salt catalyst system is used as the catalyst for selective hydrogenation of carbon-carbon double bonds (C=C) in an α,β-unsaturated ester molecule is shown below as reaction scheme (3): The reaction selectively reduces the double bonds in the acrylic acid portions of the N,N-di(propenoic acid)-4-aminobiphenyl (Compound B) to produce N,N-di(propanoic acid)-4-aminobiphenyl (Compound C).

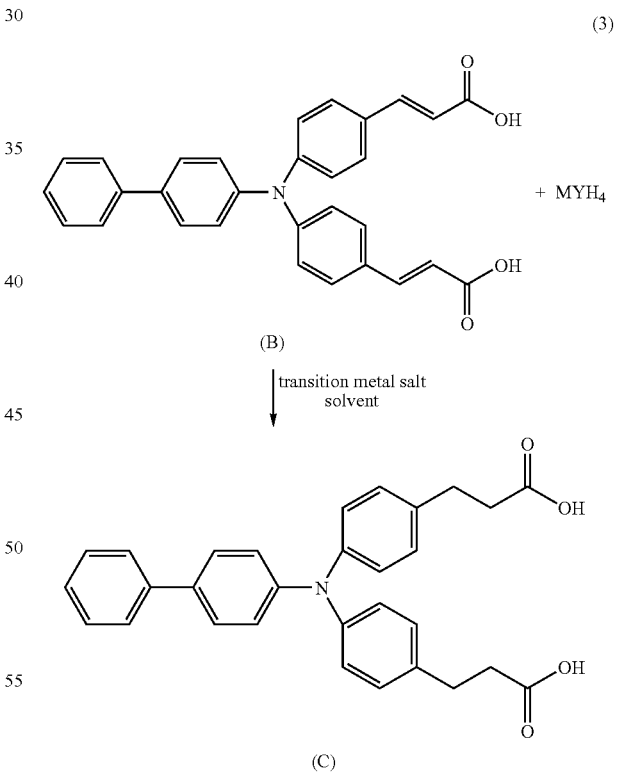

In embodiments, the catalyst may be included in amounts from about 2 to about 25% by weight, or from about 5 to about 15% by weight, based on the total weight of the reactants, i.e. based on the total weight of acceptor molecules, hydrogen donor molecules and catalyst.

The catalytic transfer hydrogenation reaction of embodiments may be carried out in any suitable organic solvent or mixture of organic solvents. Suitable organic solvents include, for example, alcohols such as methanol, ethanol, isopropanol and the like; alkanes, such as hexane, decane and the like ethers, such as diethyl ether, tetrahydrofuran, dimethoxyethane and the like; aromatic solvents, such as toluene, xylene, and the like; and mixtures thereof. The choice of specific solvent or mixture of solvents can be decided based on the solubility of the starting materials, intermediates and final products, and will be readily apparent or within routine experimentation to those skilled in the art. Solvents may, be chosen based on the desired operating temperature range.

In embodiments, the solvent may be included in any suitable amount. In particular, solvent may be present in amounts from about 1 to about 99%, or from about 25 to about 75% by weight, based on the total weight of the reactants. The amount of solvent can be readily determined by one of ordinary skill in the art, based on the amount of solvent necessary to dissolve the reactants.

Temperature may affect catalytic transfer hydrogenation in embodiments. For example, at higher temperatures (such as about 300° C. to about 350° C.), catalytic hydrogen transfer may be used to form aromatic groups. See, for example, Brieger, II. C. However, the reactions of embodiments may be carried out at temperatures of from about 0° C. to about 100° C., such as from about 25° C. to about 85° C. and from about 50° C. to about 65° C. The reaction temperature of embodiments may be selected to correspond to temperature at which the donor molecule may be oxidized, as described above.

The reaction is carried out in the presence of the catalyst, and can be conducted in batch or continuous mode. However, in embodiments, the reaction is conducted in batch mode. For example, the reaction can be carried out for from about 30 minutes to about 15 hours, such as from about 45 minutes to about 10 hours, although a reaction time of from about 1 hour to about 2 hours is suitable in embodiments. The reaction of embodiments may be carried out with stirring.

In the catalytic transfer hydrogenation reactions of embodiments, hydrogen gas is produced in-situ at low levels as a reaction by-product, as discussed above. Hydrogen gas production is proportional to the amount of hydrogen donor used, and a hydrogen atmosphere is not necessary for successful practice of embodiments. Because a hydrogen atmosphere is not required, the processes of embodiments can be practiced with greater production efficiency and safety than processes involving hydrogenation by compressed hydrogen gas. The processes of embodiments can achieve greater production efficiency, because standard reaction vessels may be used, without allowances for hydrogen gas volume in the reaction vessel. Processes of embodiments also increase safety because the low levels of hydrogen gas produced may be diluted with air or nitrogen and safely vented to the atmosphere, which can eliminate the need for special safety classifications within a production plant.

In addition, donor molecules suitable for use in embodiments generally present fewer safety risks. For example, one suitable donor molecule, ammonium formate, has a slightly higher health hazard rating than hydrogen gas. However, hydrogen gas has a much greater flammability than ammonium formate, as illustrated by their respective National Fire Protection Association ratings, shown in Table 1.

TABLE 1

|  | Health | Flammability | Reactivity |
|---|---|---|---|
| Hydrogen | 0 | 4 | 0 |
| Ammonium Formate | 1 | 0 | 0 |

After the reaction of embodiments is completed, suitable separation, filtration, and/or purification processes can be conducted, as desired to a desired purity level. For example, the desired arylamine product can be subjected to conventional organic washing steps, can be separated, can be decolorized (if necessary), treated with known absorbents (such as silica, alumina and clays, if necessary) and the like. The final product can be isolated, for example, by a suitable recrystallization procedure. The final product can also be dried, for example, by air drying, vacuum drying, or the like. All of these procedures are conventional and will be apparent to those skilled in the art.

The arylamine produced by this process can itself be used as a final product, or it can be further processed and/or reacted to provide other compounds for their separate use. For example, the arylamine can be used itself as a charge-transport material in an electrostatographic imaging member, or it can be further processed and/or reacted to provide other charge-transport materials or other compounds useful in such electrostatographic imaging member. An exemplary electrostatographic imaging member will now be described in greater detail.

In electrophotographic photoreceptors of embodiments, the photoreceptors can include various layers such as undercoating layers, charge-generating layers, charge-transport layers, overcoat layers, and the like. The overcoating layers of embodiments can be a silicon-overcoat layer, which can comprise one or more silicon compounds, a resin, and a charge-transport molecule such as an arylamine.

In embodiments, the resin may be a resin soluble in a liquid component in a coating solution used for formation of a silicon-overcoat layer. Such a resin soluble in the liquid component may be selected based upon the kind of liquid component. For example, if the coating solution contains an alcoholic solvent, a polyvinyl acetal resin such as a polyvinyl butyral resin, a polyvinyl formal resin or a partially acetalized polyvinyl acetal resin in which butyral is partially modified with formal or acetoacetal, a polyamide resin, a cellulose resin such as ethyl cellulose and a phenol resin may be suitably chosen as the alcohol-soluble resins. These resins may be used either alone or as a combination of two or more resins. Of the above-mentioned resins, the polyvinyl acetal resin is particularly suitable in embodiments in terms of electric characteristics.

In embodiments, the weight-average molecular weight of the resin soluble in the liquid component may be from about 2,000 to about 1,000,000, such as from about 5,000 to about 50,000. When the weight-average molecular weight is less than about 2,000, enhancing discharge-gas resistance, mechanical strength, scratch resistance, particle dispersibility, etc., tend to become insufficient. However, when the weight-average molecular weight exceeds about 1,000,000, the resin solubility in the coating solution decreases, and the amount of resin added to the coating solution may be limited and poor film formation in the production of the photosensitive layer may result.

Further, the amount of the resin soluble in the liquid component may be, in embodiments, from about 0.1 to about 15% by weight, or from about 0.5 to about 10% by weight, based on the total amount of the coating solution. When the amount added is less than 0.1% by weight, enhancing discharge-gas resistance, mechanical strength, scratch resistance, particle dispersibility, etc., tend to become insufficient. However, if the amount of the resin soluble in the liquid component exceeds about 15% by weight, there is a tendency for formation of indistinct images when the electrophotographic photoreceptor of the disclosure is used at high temperature and high humidity.

There is no particular limitation on the silicon compound used in embodiments of the disclosure, as long as it has at least one silicon atom. However, a compound having two or more silicon atoms in its molecule may be used in embodiments. The use of the compound having two or more silicon atoms in its molecule allows both the strength and image quality of the electrophotographic photoreceptor to be achieved at higher levels.

Further, in embodiments, the silicon compounds may include silane coupling agents such as a tetrafunctional alkoxysilane, such as tetramethoxysilane, tetraethoxysilane and the like; a trifunctional alkoxysilane such as methyltrimethoxy-silane, methyl triethoxysilane, ethyltrimethoxysilane, methyltrimethoxyethoxysilane, vinyltrimethoxysilane, vinyltriethoxysilane, phenyltrimethoxysilane, γ-glycidoxypropylmethyldiethoxysilane, γ-glycidoxypropyltrimethoxysilane, γ-glycidoxypropyl-triethoxysilane, γ-aminopropyltriethoxysilane, γ-aminopropyltrimethoxysilane, γ-aminopropylmethyldimethoxysilane, N-β-(aminoethyl)-γ-aminopropyltriethoxy-silane, (tridecafluoro-1,1,2,2-tetrahydrooctyl)triethoxysilane, (3,3,3-trifluoropropyl)-trimethoxysilane, 3-(heptafluoroisopropoxy)propyltriethoxysilane, 1H,1H,2H ,2H-perfluoroalkyltriethoxysilane, 1H,1H,2H, 2H-perfluorodecyltriethoxysilane or 1H,1H,2H,2H-perfluorooctyltriethoxysilane; a bifunctional alkoxysilane such as dimethyldimethoxysilane, diphenyldimethoxysilane or methylphenyldimethoxysilane; and a monofunctional alkoxysilane such as trimethylmethoxysilane. In order to improve the strength of the photosensitive layer, trifunctional alkoxysilanes and tetrafunctional alkoxysilanes may be used in embodiments, and in order to improve the flexibility and film-forming properties, monofunctional alkoxysilanes and bifunctional alkoxysilanes may be used in embodiments.

Silicone hard-coating agents containing these coupling agents can also be used in embodiments. Commercially available hard-coating agents include KP-85, X-40-9740 and X-40-2239 (available from Shinetsu Silicone Co., Ltd.), and AY42-440, AY42-441 and AY49-208 (available from Toray Dow Corning Co., Ltd.).

Various fine particles can also be added to the silicon compound-containing layer, for example, to further improve the stain adhesion resistance and lubricity of embodiments of the electrophotographic photoreceptor. The fine particles may be used either alone or as a combination of two or more such fine particles. Non-limiting examples of the fine particles include fine particles containing silicon, such as fine particles containing silicon as a constituent element, and specifically include colloidal silica and fine silicone particles. The content of the fine silicone particles in the silicon-containing layer of embodiments may be within the range of 0.1 to 20% by weight, or within the range of 0.5 to 10% by weight, based on the total solid content of the silicon-containing layer.

Colloidal silica used in embodiments as the fine particles containing silicon in the disclosure is selected from an acidic or alkaline aqueous dispersion of the fine particles having an average particle size of 1 to 100 nm, or 10 to 30 nm, and a dispersion of the fine particles in an organic solvent, such as an alcohol, a ketone or an ester, and generally, commercially available particles can be used.

There is no particular limitation on the solid content of colloidal silica in a top-surface layer of the electrophotographic photoreceptor of embodiments. However, in embodiments, colloidal silica may be included in amounts of from about 1 to about 50% by weight, such as from about 5 to about 30% by weight, based on the total solid content of the top surface layer, in terms of film forming properties, electric characteristics and strength.

The fine silicone particles used as the fine particles containing silicon in the disclosure may be selected from silicone resin particles, silicone rubber particles and silica particles surface-treated with silicone, which are spherical and have an average particle size of from about 1 to 500 nm, such as from about 10 to about 100 nm, and generally, commercially available particles can be used in embodiments.

In embodiments, the fine silicone particles are small-sized particles that are chemically inactive and excellent in dispersibility in a resin, and further are low in content as may be necessary for obtaining sufficient characteristics. Accordingly, the surface properties of the electrophotographic photoreceptor can be improved without inhibition of the cross-linking reaction. That is to say, fine silicone particles improve the lubricity and water repellency of electrophotographic photoreceptor surfaces where incorporated into strong cross-linked structures, which may then be able to maintain good wear resistance and stain-adhesion resistance for a long period of time. The content of the fine silicone particles in the silicon compound-containing layer of embodiments may be from about 0.1 to about 20% by weight, such as from about 0.5 to about 10% by weight, based on the total solid content of the silicon compound-containing layer.

Other fine particles that may be used in embodiments include fine fluorine-based particles such as ethylene tetrafluoride, ethylene trifluoride, propylene hexafluoride, vinyl fluoride and vinylidene fluoride, and semiconductive metal oxides such as $ZnO$—$Al_2O_3$, $SnO_2$—$Sb_2O_3$, $In_2O_3$—$SnO_2$, $ZnO$—$TiO_2$, $MgO$—$Al_2O_3$, $FeO$—$TiO_2$, $TiO_2$, $SnO_2$, $In_2O_3$, $ZnO$ and $MgO$.

In conventional electrophotographic photoreceptors, when the above-mentioned fine particles are contained in the photosensitive layer, the compatibility of the fine particles with a charge-transport substance or a binding resin may become insufficient, which causes layer separation in the photosensitive layer, and thus the formation of an opaque film. As a result, the electric characteristics have deteriorated in some cases. In contrast, the silicon compound-containing layer of embodiments (a charge-transport layer in this case) may contain the resin soluble in the liquid component in the coating solution used for formation of this layer and the silicon compound, thereby improving the dispersibility of the fine particles in the silicon compound-containing layer. Accordingly, the pot life of the coating solution maybe sufficiently prolonged, and deterioration of the electric characteristics may be prevented.

Further, an additive such as a plasticizer, a surface modifier, an antioxidant, or an agent for preventing deterioration by light can also be used in the silicon compound-containing layer of embodiments. Non-limiting examples of plasticizers that may be used in embodiments include, for example, biphenyl, biphenyl chloride, terphenyl, dibutyl phthalate, diethylene glycol phthalate, dioctyl phthalate, triphenylphosphoric acid, methylnaphthalene, benzophenone, chlorinated paraffin, polypropylene, polystyrene and various fluorohydrocarbons.

The antioxidants may include an antioxidant having a hindered-phenol, hindered-amine, thioether or phosphite partial structure. This is effective for improvement of potential stability and image quality in environmental variation. The antioxidants include an antioxidant having a hindered-phenol, hindered-amine, thioether or phosphite partial structure. This is effective for improvement of potential stability and image quality in environmental variation. For example, the hindered-phenol antioxidants include SUMILIZER BHT-R, SUMILIZER MDP-S. SUMILIZER BBM-S, SUMILIZER WX-R, SUMILIZER NW, SUMILIZER BP-76, SUMILIZER BP-101, SUMILIZER GA-80, SUMILIZER GM and SUMILIZER GS (the above are manufactured by Sumitomo Chemical Co., Ltd.), IRGANOX 1010, IRGANOX 1035, IRGANOX 1076, IRGANOX 1098, IRGANOX 1135, IRGANOX 1141, IRGANOX 1222, IRGANOX 1330, IRGANOX 1425WLj, IRGANOX 1520Lj, IRGANOX 245, IRGANOX 259, IRGANOX 3114, IRGANOX 3790, IRGANOX 5057 and IRGANOX 565 (the above are manufactured by Ciba Specialty Chemicals), and ADECASTAB AO-20, ADECASTAB AO-30, ADECASTAB AO-40, ADECASTAB AO-50, ADECASTAB AO-60, ADECASTAB AO-70, ADECASTAB AO-80 and ADECASTAB AO-330i (the above are manufactured by Asahi Denka Co., Ltd.). The hindered-amine antioxidants include SANOL LS2626, SANOL LS765, SANOL LS770, SANOL LS744, TINUVIN 144, TINUVIN 622LD, MARK LA57, MARK LA67, MARK LA62, MARK LA68, MARK LA63 and SUMILIZER TPS, and the phosphite antioxidants include MARK 2112, MARK PEP.8, MARK PEP-24G, MARK PEP.36, MARK 329K and MARK HP-10. Of these, hindered-phenol and hindered-amine antioxidants may be particularly suitable, in embodiments.

There is no particular limitation on the thickness of the silicon-containing layer, however, in embodiments, the silicon-containing layer may be from about 2 to about 5 μm in thickness, such as from about 2.7 to about 3.2 μm in thickness.

The electrophotographic photoreceptor of embodiments may be either a function-separation-type photoreceptor, in which a layer containing a charge-generation substance (charge-generation layer) and a layer containing a charge-transport substance (charge-transport layer) are separately provided, or a monolayer-type photoreceptor, in which both the charge-generation layer and the charge-transport layer are contained in the same layer, as long as the electrophotographic photoreceptor of the particular embodiment has the photosensitive layer provided with the above-mentioned silicon compound-containing layer. The electrophotographic photoreceptor will be described in greater detail below, taking the function-separation-type photoreceptor as an example.

FIG. 1 is a cross-sectional view schematically showing an embodiment of the electrophotographic photoreceptor of the disclosure. The electrophotographic photoreceptor 1 shown in FIG. 1 is a function-separation-type photoreceptor in which a charge-generation layer 13 and a charge-transport layer 14 are separately provided. That is, an underlayer 12, the charge-generation layer 13, the charge transport layer 14 and a protective layer 15 are laminated onto a conductive support 11 to form a photosensitive layer 16. The protective layer 15 contains a resin soluble in the liquid component contained in the coating solution used for formation of this layer and the silicon compound. The various layers of the photoreceptor shown in FIG. 1 are generally known, and are described in detail in the above-mentioned commonly owned and co-pending applications.

The electrophotographic photoreceptor of embodiments should not be construed as being limited to the above-mentioned constitution. For example, the electrophotographic photoreceptor shown in FIG. 1 is provided with the protective layer 15. However, when the charge-transport layer 14 contains the resin soluble in the liquid component in the coating solution used for formation of this layer and the silicon compound, the charge-transport layer 14 may be used as a top surface layer (a layer on the side farthest apart from the support 11) without using the protective layer 15. In this case, the charge-transport substance contained in the charge-transport layer 14 is desirably soluble in the liquid component in the coating solution used for formation of the charge-transport layer 14. For example, when the coating solution used for formation of the charge-transport layer 14 contains an alcohol solvent, the silicon compounds described above, including arylamine derivatives prepared by processes that include selective hydrogenation by catalytic transfer, can be used as the charge-transport substances. In embodiments, a particularly suitable charge-transport molecule is the following arylamine (Compound D), which may be produced from Compound C above:

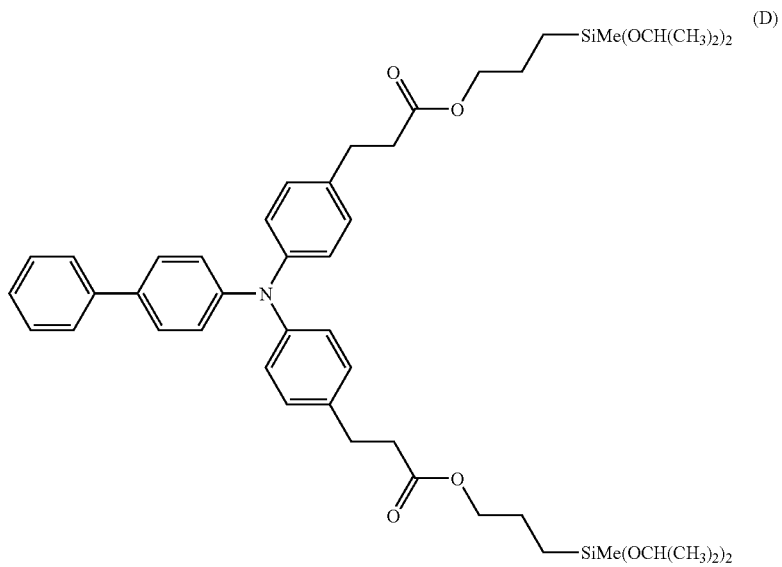

Figure 3:
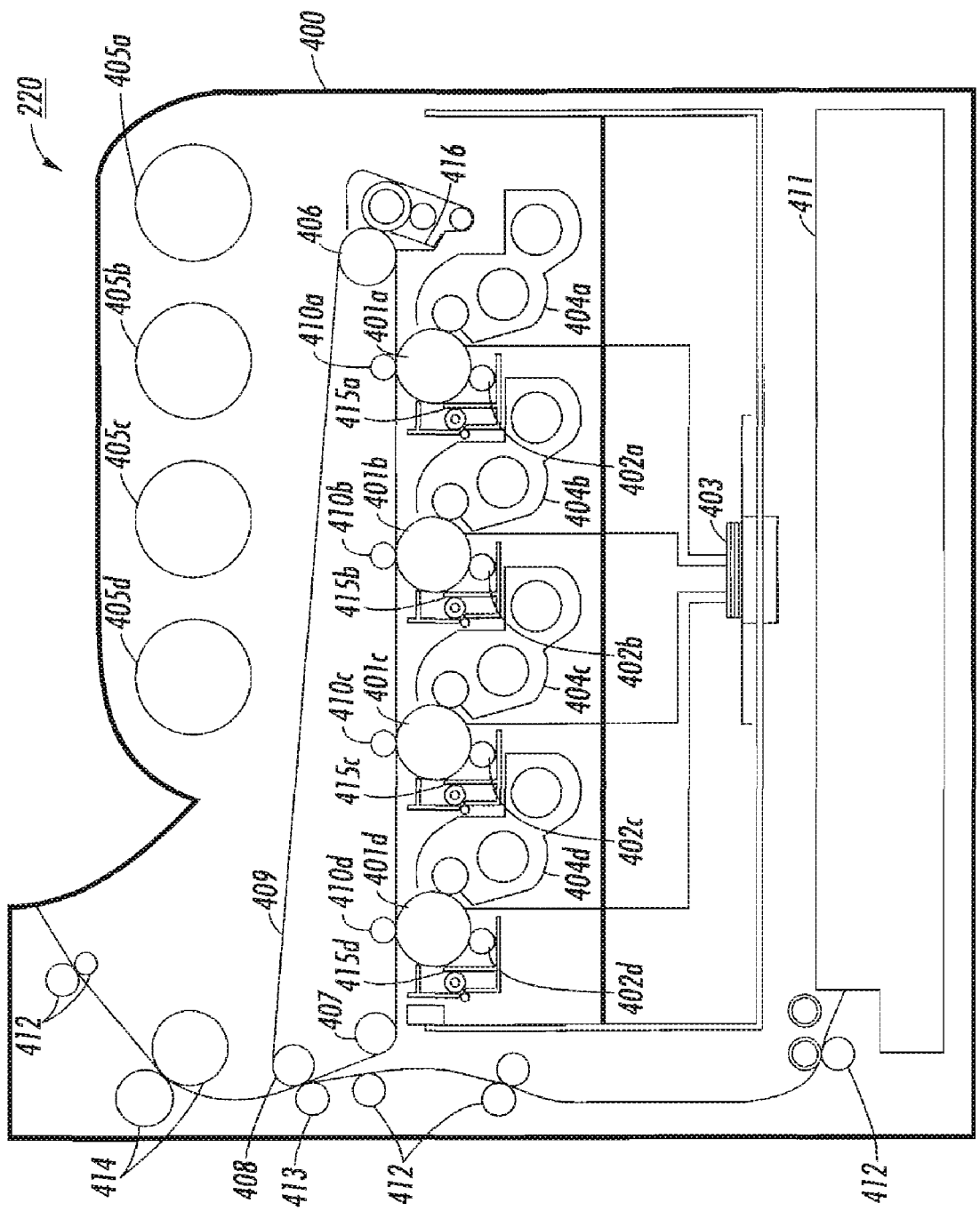
FIG. 3 is a schematic view showing another embodiment of an image-forming apparatus of the disclosure.

FIG. 3 is a cross-sectional view showing another exemplary embodiment of an image-forming apparatus. The image-forming apparatus 220 shown in FIG. 3 is an image-forming apparatus of an intermediate-transfer system, and four electrophotographic photoreceptors 401a to 401d are arranged in parallel with each other along an intermediate-transfer belt 409 in a housing 400.

Here, the electrophotographic photoreceptors 401a to 401d carried by the image-forming apparatus 220 are each the electrophotographic photoreceptors. Each of the electrophotographic photoreceptors 401a to 401d may rotate in a predetermined direction (counterclockwise on the sheet of FIG. 3), and charging rolls 402a to 402d, developing device 404a to 404d, primary transfer rolls 410a to 410d and cleaning blades 415a to 415d are each arranged along the rotational direction thereof. In each of the developing device 404a to 404d, four-color toners of yellow (Y), magenta (M), cyan (C) and black (B) contained in toner cartridges 405a to 405d can be supplied, and the primary transfer rolls 410a to 410d are each brought into abutting contact with the electrophotographic photoreceptors 401a to 401d through an intermediate-transfer belt 409.

Further, a laser-light source (exposure unit) 403 is arranged at a specified position in the housing 400, and it is possible to irradiate surfaces of the electrophotographic photoreceptors 401a to 401d after charging with laser light emitted from the laser-light source 403. This performs the respective steps of charging, exposure, development, primary transfer and cleaning in turn in the rotation step of the electrophotographic photoreceptors 401a to 401d, and toner images of the respective colors are transferred onto the intermediate-transfer belt 409, one over the other.

The intermediate-transfer belt 409 is supported with a driving roll 406, a backup roll 408 and a tension roll 407 at a specified tension, and rotatable by the rotation of these rolls without the occurrence of deflection. Further, a secondary transfer roll 413 is arranged so that it is brought into abutting contact with the backup roll 408 through the intermediate-transfer belt 409. The intermediate-transfer belt 409, which has passed between the backup roll 408 and the secondary transfer roll 413, is cleaned up by a cleaning blade 416, and then repeatedly subjected to the subsequent image-formation process.

Further, a tray (tray for a medium to which a toner image is to be transferred) 411 is provided at a specified position in the housing 400. The medium to which the toner image is to be transferred (such as paper) in the tray 411 is conveyed in turn between the intermediate-transfer belt 409 and the secondary transfer roll 413, and further between two fixing rolls 414 brought into abutting contact with each other, with a conveying roll 412, and then delivered out of the housing 400.

According to the exemplary image-forming apparatus 220 shown in FIG. 3, the use of electrophotographic photoreceptors of embodiments as electrophotographic photoreceptors 401a to 401d may achieve discharge gas resistance, mechanical strength, scratch resistance, etc. on a sufficiently high level in the image-formation process of each of the electrophotographic photoreceptors 401a to 401d. Accordingly, even when the photoreceptors are used together with the contact-charging devices or the cleaning blades, or further with the spherical toner obtained by chemical polymerization, good image quality can be obtained without the occurrence of image defects such as fogging. Therefore, also according to the image-forming apparatus for color-image formation using the intermediate-transfer body, such as this embodiment, the image-forming apparatus, which can stably provide good image quality for a long period of time, is realized.

Figure 2:
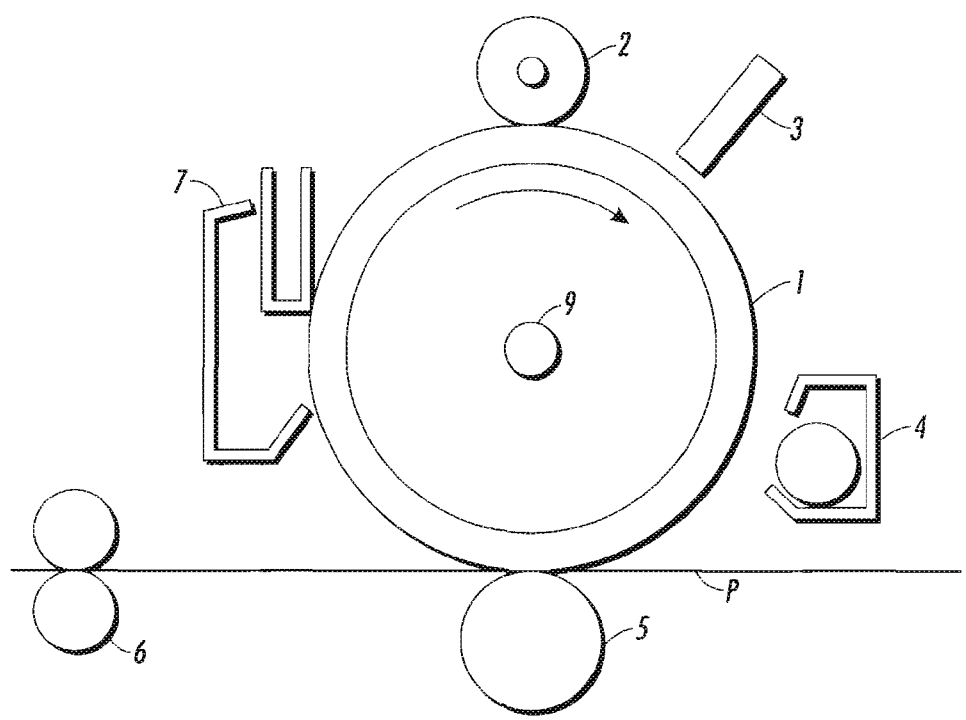
FIG. 2 is a schematic view showing an embodiment of an image-forming apparatus of the disclosure.

The disclosure should not be construed as being limited to the above-mentioned embodiments. For example, each apparatus shown in FIG. 2 or 3 may be equipped with a process cartridge comprising the electrophotographic photoreceptor 1 (or the electrophotographic photoreceptors 401a to 401d) and charging device 2 (or the charging devices 402a to 402d). The use of such a process cartridge allows maintenance to be performed more simply and easily.

Further, in embodiments, when a charging device of the non-contact charging system such as a corotron charger is used in place of the contact-charging device 2 (or the contact-charging devices 402a to 402d), sufficiently good image quality can be obtained.

Specific examples are described in detail below. These examples are intended to be illustrative, and the materials, conditions, and process parameters set forth in these exemplary embodiments are not limiting. All parts and percentages are by weight unless otherwise indicated.

EXAMPLES

Example 1

Small-Scale Pd/C-Catalyzed Hydrogenation of N,N-di(propenoic acid)-4-aminobiphenyl (Compound B)

Into a test tube, the following was charged: 0.15 grams (0.325 mmol) of N,N-di; propenoic acid)-4-aminobiphenyl (Compound B), 0.154 grams (2.44 mmol) of ammonium formate, 0.0376 grams of 10% palladium on charcoal (Pd/C), and 2 mL of methanol. The mixture was heated to reflux in a water bath, at which point the first sample was drawn. Samples were drawn every 10 minutes for 60 minutes. The reaction was monitored by thin layer chromatography and was found to be complete after 60 minutes at reflux (~65° C.). The reaction solution was cooled and filtered. The solvent was removed under nitrogen. The solid residue was washed with 2 mL of 1 Molar HCl and redissolved in 8 mL of ethyl acetate. The ethyl acetate was removed under nitrogen. $^1$H NMR analysis showed that N,N-di(propanoic acid)-4-amino-biphenyl (Compound C) was produced.

Example 2

Larger-Scale Pd/C-Catalyzed Hydrogenation of N,N-di(propenoic acid)-4-aminobiphenyl (Compound B)

Into a 500-mL round-bottom flask, the following was charged: 10.0 grams (21.667 mmol) of N,N-di(propenoic acid)-4-aminobiphenyl (Compound B), 10.25 grams of ammonium formate, 2.5 grams of 10% palladium on charcoal (Pd/C), 200 mL of methanol and 50 mL of tetrahydrofuran. The mixture was heated to reflux in a water bath, at which point the first sample was drawn. Samples were drawn every 15 minutes for 60 minutes. The reaction was monitored by thin layer chromatography and was found to be complete after 60 minutes at reflux (~65° C.). The reaction solution was cooled and filtered. The solvent was removed under nitrogen. The solid residue was washed with water and dried. The ethyl acetate was removed under nitrogen. $^1$H NMR analysis showed that N,N-di(propanoic acid)-4-aminobiphenyl (Compound C) was produced.

Figure 4:
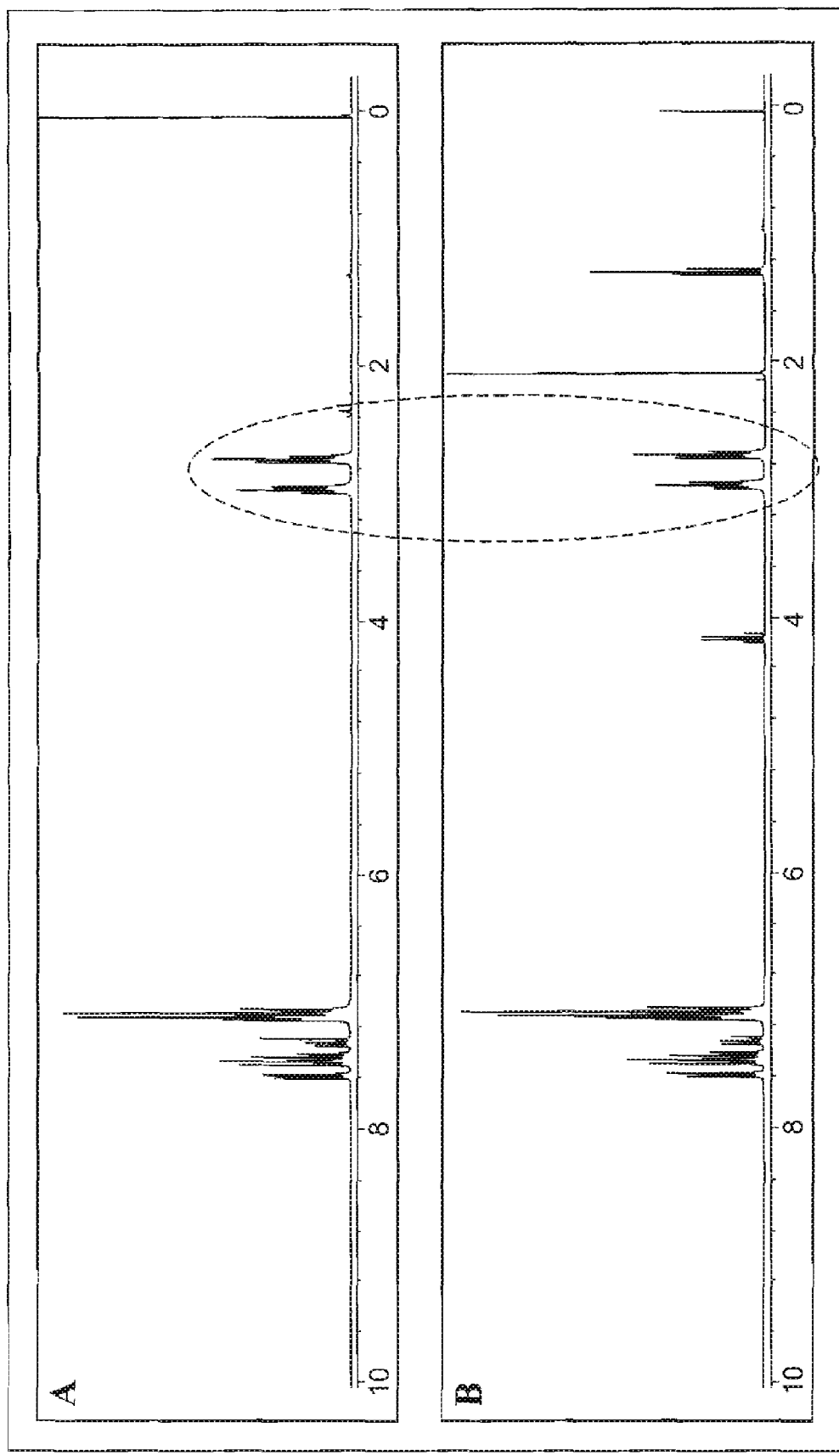
FIGS. 4(A) and 4(B) are proton nuclear magnetic resonance ($^1$H-NMR) spectrographs of products of exemplary processes.

FIGS. 4A and 4B respectively show the $^1$H NMR spectrographs corresponding to Compound C produced using compressed hydrogen gas and to Compound C produced in Example 2 (sample contained ethyl acetate residues). The circled peaks indicate the reduction of the double bonds.

Example 3

Metal Hydride—Transition Metal Salt Catalyst System Catalyzed Hydrogenation of N,N-di(propenoic acid)-4-aminobiphenyl (Compound B)

Into a 250-mL round-bottom flask, the following was charged: 9.8 grams (0.02 mol) of N,N-di(propenoic acid)-4-aminobiphenyl (Compound B), 65 grams of methanol, 40 grams of tetrahydrofuran, and 0.475 grams (0.002 mol) of NiCl. The mixture was homogenized. After homogenization, 1.5 grams (0.04 mol) of NaBH$_4$ was added slowly. Hydrogen gas was produced, and black solids precipitated. The reaction mixture was stirred at room temperature for 60 minutes, after which the black solid precipitate was removed by filtration. The filtrate was condensed under nitrogen, dissolved in diethyl ether, and washed with water. After drying with magnesium sulfate (MgSO$_4$), the diethyl ether was removed under nitrogen, and pale yellow, sticky solids remained. The solids were recrystallized with a mixture of 1:1:1.5 (v/v) acetone: butanol:methanol, to yield a white powder. $^1$H NMR analysis showed that N,N-di(propanoic acid)-4-aminobiphenyl (Compound C) was produced.

Comparative Example

Hydrogenation of N,N-di(propenoic acid)-4-aminobiphenyl (Compound B)

Into a 10-L glass reactor, 1385 grams (2.83 mol) of N,N-di(propenoic acid)-4-aminobiphenyl (Compound B) was dissolved in 3 L of toluene, 2 L of methanol and 0.5 L of tetrahydrofuran. Six grams of 10% palladium on charcoal (Pd/C) were added, and the reaction vessel was placed under nitrogen atmosphere. The reaction mixture was stirred vigorously for 5 days, and the end of the reaction was determined by $^1$H NMR. The Pd/C catalyst was recovered from the reaction mixture by filtration. The reaction solution was distilled under low pressure to remove the reaction solvent mixture. 1330 grams of crude reaction product was recovered. The crude reaction product was recrystallized with 1 L of acetone, 1 L of butanol and 1.5 L of methanol to obtain 908 grams (1.84 mol) of an uncolored solid that $^1$H NMR analysis showed was N,N-di(propanoic acid)-4-aminobiphenyl (Compound C).

Figure 5:
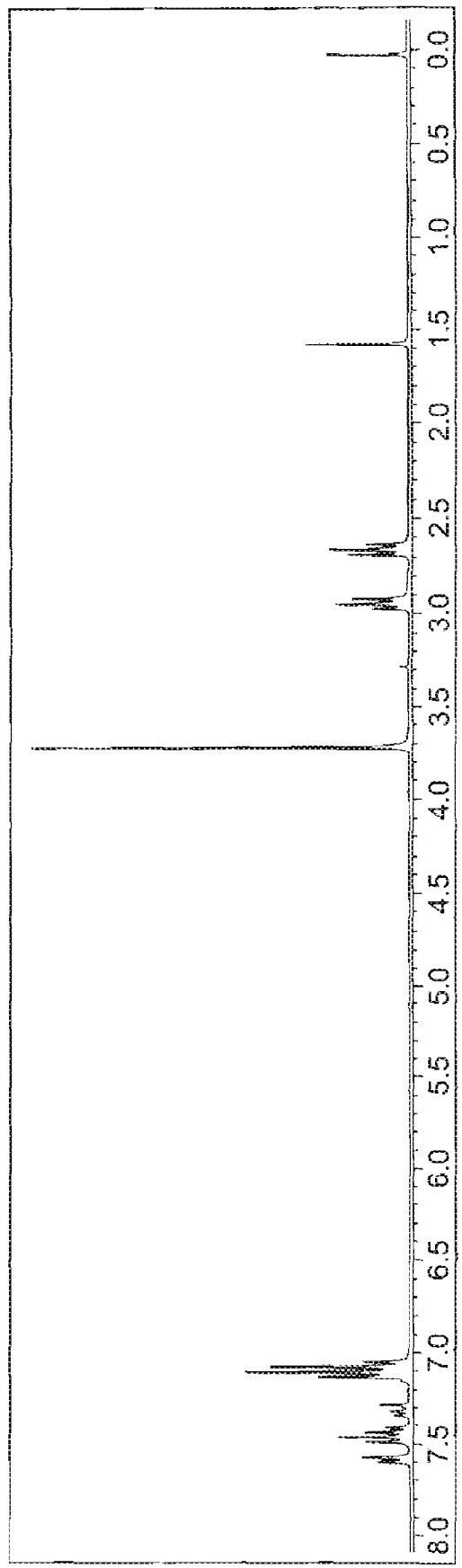
FIG. 5 is a proton nuclear magnetic resonance ($^1$H-NMR) spectrograph of a product of an exemplary process.
Figure 6:
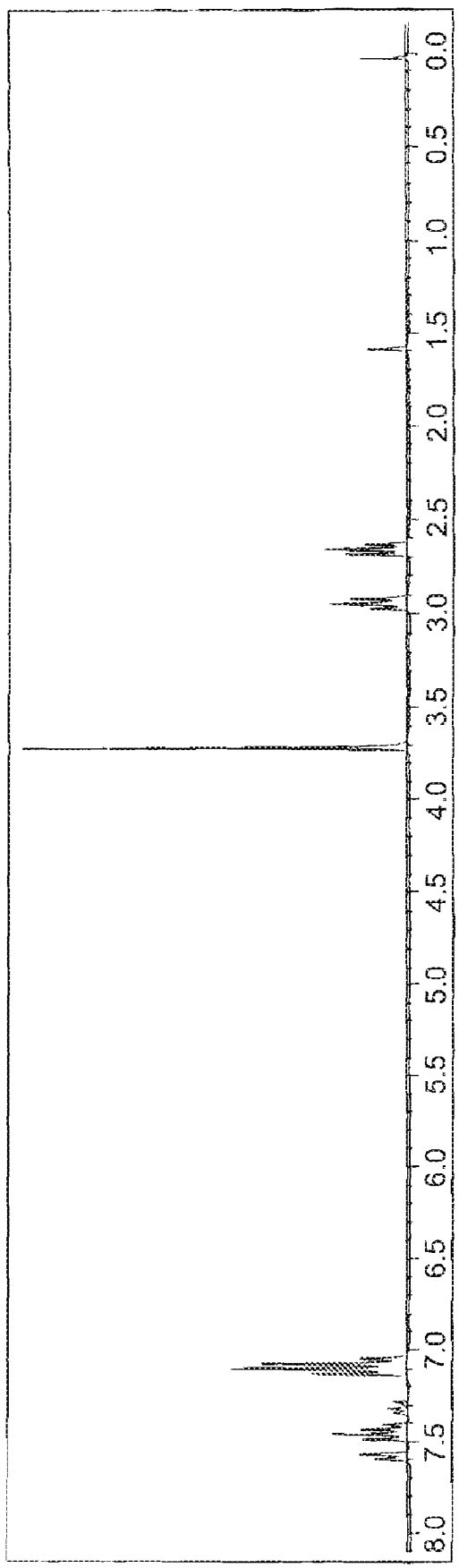
FIG. 6 is a proton nuclear magnetic resonance ($^1$H-NMR) spectrograph of a product of an exemplary process.

FIGS. 5 and 6 respectively show the $^1$H NMR spectrographs corresponding to Compound C produced in Example 3 and to Compound C produced in the Comparative Example.

It will be appreciated that various of the above-discussed and other features and functions, or alternatives thereof) may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A process for selectively hydrogenating unsaturated carbon bonds in organic molecules, comprising:

providing at least one disubstituted 4-aminobiphenyl compound having the formula:

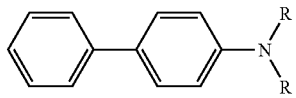

wherein R is comprised of a phenyl moiety with a side chain that contains an unsaturated carbon bond and a carboxylic group, providing one or more hydrogen donor molecules; and hydrogenating the unsaturated carbon bond of the at least one disubstituted 4-aminobiphenyl compound in the presence of one or more catalysts.

2. The process according to claim 1, wherein the at least one disubstituted 4-aminobiphenyl compound is a N,N-di(alkylacrylic acid)-4-aminobiphenyl compound.

3. The process according to claim 1, wherein said hydrogen donor molecule is present an amount of from about 1 to about 4 molar equivalents, based on an amount of the disubstituted 4-aminobiphenyl compound.

4. The process according to claim 1, wherein said hydrogen donor molecule is one or more donor molecule selected from the group consisting of hydrazine, formic acid, formates, substituted and unsubstituted cyclohexenes, substituted and unsubstituted octalins, substituted and unsubstituted tetralins, substituted and unsubstituted pinenes, substituted and unsubstituted careens, substituted and unsubstituted phellandrenes, substituted and unsubstituted terpinolenes, substituted and unsubstituted menthenes, substituted and unsubstituted cadalene, substituted and unsubstituted pulegones, substituted and unsubstituted selinenes, alcohols, and mixtures thereof.

5. The process according to claim 4, wherein said hydrogen donor molecule is ammonium formate.

6. The process according to claim 1, wherein said catalyst is one or more catalyst selected from the group consisting of palladium-based catalysts; Pt black, Pt/C, Raney Ni, RuCl$_2$(Ph$_3$P)$_3$, HIrCl$_2$(Me$_2$SO)$_3$, Ir(CO)Br(Ph$_3$P)$_2$, RhCl(Ph$_3$As)$_2$, PtCl$_2$(Ph$_3$As)$_2$+SnCl$_2$.H$_2$O, and mixtures thereof.

7. The process according to claim 6, wherein said catalyst is one or more catalyst selected from the group consisting of palladium-based catalysts and mixtures thereof.

8. The process according to claim 6, wherein said catalyst is one or more catalyst selected from the group consisting of Pd black, Pd/C, Pd/CaCO$_3$, Pd/Al$_2$O$_3$Pd/Pt, ligated palladium catalysts, Pt black, Pt/C, Raney Ni, and mixtures thereof.

9. The process according to claim 1, wherein said catalyst is one or more catalyst selected from the group consisting of metal hydride-transition metal salt catalyst systems, and mixtures thereof.

10. The process according to claim 9, wherein said metal hydride-transition metal salt catalyst systems comprises a metal hydride selected from the group consisting of NaBH$_4$, LiBH$_4$, KBW$_4$, NH$_4$BH$_4$, (CH$_3$)$_4$NBH$_4$, NaAlH$_4$, LiAlH$_4$, KAlH$_4$, NaGaH$_4$, LiGaH$_4$, KGaH$_4$, quaternary borohydrides, ion exchange resins and mixtures thereof.

11. The process according to claim 9, wherein said metal hydride-transition metal salt catalyst systems comprises a transition metal salt that includes a transition metal selected from the group consisting of ruthenium, iron, cobalt, nickel, copper, manganese, rhodium, rhenium, platinum, palladium, chromium, silver, osmium, iridium, borides thereof, alloys thereof, and mixtures thereof.

12. The process according to claim 11, wherein said transition metal salt is selected from the group consisting of $Cu_2Cl_2$, $CuCl_2$, $CoCl_2$, $PdCl_2$, $CuSO_4$, and mixtures thereof.

13. The process according to claim 1, wherein said catalyst is present an amount of from 2 to about 25% by weight, based on the total weight of the disubstituted 4-aminobiphenyl compounds, hydrogen donor molecules and catalyst.

14. The process according to claim 1, wherein said hydrogenating is carried out at a temperature of from about 0° C. to about 100° C.

15. The process according to claim 14, wherein said hydrogenating is carried out at a temperature of from about 50° C. to about 65° C.

16. The process according to claim 1, wherein said hydrogenating is carried out in one or more organic solvent selected from the group consisting of alcohols, alkanes, ethers, aromatic solvents, and mixtures thereof.

17. The process according to claim 16, wherein said hydrogenating is carried out in one or more organic solvent selected from the group consisting of methanol, ethanol, isopropanol, hexane, decane, diethyl ether, tetrahydrofuran, dimethoxyethane, toluene, xylene, and mixtures thereof.

18. The process according to claim 1, wherein the at least one disubstituted 4-aminobiphenyl compound is a N,N-di (propenoic acid))-4-aminobiphenyl compound.

* * * * *